United States Patent
Ueno et al.

(10) Patent No.: US 6,891,072 B2
(45) Date of Patent: *May 10, 2005

(54) PROCESS FOR PRODUCTION OF DIMERS OR AROMATIC MONOHYDROXYL COMPOUNDS

(75) Inventors: Ryuzo Ueno, Nishinomiya (JP); Masaya Kitayama, Takarazuka (JP); Kenji Minami, Sennan (JP); Hiroyuki Wakamori, Hikami-gun (JP); Hikari Hirai, Sanda (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/433,908

(22) PCT Filed: Apr. 18, 2002

(86) PCT No.: PCT/JP02/03852

§ 371 (c)(1),
(2), (4) Date: Jun. 6, 2003

(87) PCT Pub. No.: WO02/085829

PCT Pub. Date: Oct. 31, 2002

(65) Prior Publication Data

US 2004/0143141 A1 Jul. 22, 2004

(30) Foreign Application Priority Data

Apr. 19, 2001 (JP) ........................................ 2001-120976

(51) Int. Cl.[7] .............................................. C07C 39/12
(52) U.S. Cl. ........................ 568/719; 552/291; 552/292; 552/304; 560/45; 560/56; 564/153; 568/730
(58) Field of Search ................................. 568/719, 730; 552/292, 291, 304; 560/45, 56; 564/153

(56) References Cited

U.S. PATENT DOCUMENTS

| 3,278,610 A | | 10/1966 | Butte, Jr. | |
| 3,631,208 A | * | 12/1971 | Hay | ........................... 568/718 |
| 4,085,124 A | * | 4/1978 | Rutledge | ..................... 552/304 |
| 4,139,544 A | * | 2/1979 | Rutledge | ..................... 552/304 |
| 2004/0063963 A1 | * | 4/2004 | Ueno et al. | .................. 548/159 |

FOREIGN PATENT DOCUMENTS

| JP | 62-77341 A | 4/1987 |
| JP | 6-145086 A | 5/1994 |
| JP | 8-20552 A | 1/1996 |
| JP | 8-245459 A | 9/1996 |
| JP | 10-204015 A | 8/1998 |

* cited by examiner

Primary Examiner—Michael L. Shippen
(74) Attorney, Agent, or Firm—Sughrue Mion, PLLC

(57) ABSTRACT

The present invention provides a method for preparing dimer of a monohydroxy aromatic compound. In the method of the present invention, oxidative coupling reaction of a monohydroxy aromatic compound represented by formula [I]:

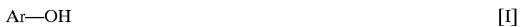

$$\text{Ar—OH} \qquad [I]$$

wherein Ar represents an optionally substituted aromatic group is carried out in a nitrogen containing polar solvent in the presence of a copper salt. By the method of the instant invention, dimer of the monohydroxy aromatic compound can be obtained in high yield.

2 Claims, 2 Drawing Sheets

PROCESS FOR PRODUCTION OF DIMERS OR AROMATIC MONOHYDROXYL COMPOUNDS

TECHNICAL FIELD

The present invention relates to a method for preparing dimer of a monohydroxy aromatic compound

BACKGROUND ART 1,1'-bi-2-naphthol, a compound obtainable by dimerization of β-naphthol or its derivative, is useful for preparing an antiseptic compound or an asymmetric synthesis catalyst.

In addition, dimers of 2-hydroxynaphthalene-3-carboxylic acid and of 2-hydroxynaphthalene-6-caboxylic acid are useful as toning agents.

U.S. Pat. No. 3,278,610 discloses a method for preparing the above described dimers, which comprises dimerizing β-naphthol in a solvent such as benzene in the presence of copper chloride, amine and oxygen.

J. Org. Chem. 1999, 64, 2264–2271 discloses a method for dimerizing β-naphthol or the like, which comprises oxidative coupling of β-naphthol, methyl 2-hydroxynaphthalene-3-carboxylate or the like in the presence of copper(I) chloride-tetramethylethylenediamine complex in dichloromethane, wherein copper(I) chloride and tetramethylethylene diamine are combined before the coupling reaction.

DISCLOSURE OF THE INVENTION

Conventional methods for preparing binaphthol derivatives require a solvent, such as benzene or dichloromethane, to dissolve β-naphthol or the like therein to facilitate the coupling reaction, and the solvent causes high cost. Further, the method of J. Org. Chem. 1999, 64, 2264–2271 is complex because the method comprises the extra step of combining copper(I) chloride and tetramethyl ethylene diamine prior to the coupling reaction.

One object of the present invention is to solve the above problems and to provide a method for preparing a binaphthol derivative in high yield with low cost.

Another object of the present invention is to provide a method useful for dimerizing not only soluble compounds, such as β-naphthol and phenol, but also hardly soluble monohydroxy aromatic compound, such as monohydroxy naphthalene dicarboxylic acid derivative.

The instant inventors intensively studied with respect to dimerization of monohydroxy aromatic compounds and have found that desired dimer of a monohydroxy aromatic compound can be obtained in high yield by carrying out the oxidative coupling reaction of said compound in a nitrogen containing polar solvent in the presence of a copper salt as a catalyst, and completed the invention.

Accordingly, the present invention provides a method for preparing dimer of a monohydroxy aromatic compound represented by formula [I]:

  [I]

wherein Ar represents an optionally substituted aromatic group,
characterized in that carrying out oxidative coupling reaction of said compound in a nitrogen containing polar solvent in the presence of a copper salt.

The reason why the present method can provide the dimer in high yield may be that the copper salt reacts with the hydroxy group of the formula [1] monohydroxy aromatic compound, the nitrogen containing polar solvent and oxygen to provide a complex having oxidizing ability, and the complex affects as a catalyst to promote the oxidative coupling reaction.

Examples of copper salts used in the present invention may include copper(I) chloride, copper(II) chloride, copper (I) bromide, copper(II) bromide, copper(I) iodide, copper(II) acetate and copper (II) formate. Copper(I) chloride is most preferable among them, since its catalytic ability is recovered by oxygen during the reaction and accordingly the amount of the copper salt used in the reaction can be reduced.

When copper(I) chloride is used, it is recommendable to supply air or oxygen actively into the reaction.

The amount of copper salt used in the reaction may be 0.5–100 mole, preferably, 5–10 mole per 100 mole of the formula [1] monohydroxy aromatic compound.

When the amount of copper salt is less than 0.5 mole per 100 mole of the monohydroxy aromatic compound, the reaction speed may become very slow, and when the amount is more than 100 mole, an unfavorable side reaction may occur.

In the method of the instant invention, the nitrogen containing polar solvent plays roles as a reaction medium to facilitate the reaction and also as a ligand which forms a complex having an oxidative ability with the copper salt. Preferable nitrogen containing polar solvents may be those represented by formulae [III] and [IV].

wherein $R_1$, $R_2$, $R_3$ and $R_4$ may be same or different and each is independently selected from the group consisting of formyl, alkyl, alkenyl, acyl and optionally substituted phenyl groups.

Examples of $R_1$, $R_2$, $R_3$ and $R_4$ may include formyl, alkyl of 1–6 carbon atoms such as methyl, ethyl, propyl and hexyl; alkenyl of 2–6 carbon atoms such as vinyl, allyl and pentenyl, acyl of 1–6 carbon atoms such as acetyl group and optionally substituted phenyl.

Examples of the substituent may include halogen atom, halogenated lower alkyl, lower alkyl, lower alkoxy such as methoxy, phenyl, naphthyl, phenoxy, furyl, amino, toluidylamino, triazylamino, pyrimidylamino, benzoylamino, hydroxy, esterified carboxyl group such as alkoxycarbonyl and phenoxycarbonyl groups, amidated carboxyl group such as phenylcarbamoyl group, alkylaminosulfonyl group and alkenyl group of 2–6 carbon atoms which may contain aryl group.

When the substituent contains an aromatic ring, the compound may further have one or more substituents such as halogen atom, lower alkyl, lower alkoxy and phenyl on said aromatic ring.

Examples of the solvent represented by formula [III] may include N,N-dimethylformamide, N,N-dimethylacetamide, N,N-diethylacetaminde, N,N-dimethylpropyoamide, N-methylacetanilide, N,N-dimethylaniline and N,N-dimethylanisidine. Examples of solvent represented by formula [IV] may contain tetramethylurea and tetraethylurea.

Preferable nitrogen containing polar solvent may include N,N-dimethylformamide, N,N-dimethylacetamide, N-methyl-2-pyrrolidone, morpholine, N-methylmorpholine, N,N-diethylacetamide, N,N-dimethylpropyoamide, tetramethylurea, tetraethylurea, N-methylacetanilide, N,N-dimethylaniline, N,N-dimethylanisidine, pyridine, and 2-methylpyridine. Especially, N,N-dimethylformamide, N,N-dimethylacetaminde and N-methyl-2-pyrrolidone are preferable since they can dissolve the hardly soluble ester or amide derivative of 2-hydroxynaphthalene-3,6-dicarboxylic acid well.

An amount of the nitrogen containing polar solvent enough to dissolve the monohydroxyaromatic compound of formula [I] may be used for the reaction. Typically, the amount may be 5–50, preferably 5–20, more preferably 5–10, fold by weight of the formula [I] monohydroxy aromatic compound.

The method of the present invention may be carried out as follows.

Firstly, the monohydroxyaromatic compound of formula [I] is dissolved or dispersed in a nitrogen containing polar solvent at room temperature. A copper salt is added thereto and the obtained reaction mixture is then heated to 40–120° C., preferably 60–80° C. under a pressurized or a normal pressure condition to undergo the oxidative coupling reaction so that dimer of the monohydroxyaromatic compound is obtained.

The duration of the oxidative coupling reaction may be determined depending on the amount of the catalyst and the reaction temperature. Generally, the reaction time may be 1–48 hours. The completion of the reaction may be confirmed by disappearance of the starting material in the reaction mixture, which can be monitored with HPLC or the like.

After the oxidative coupling reaction is completed, the reaction solution or that admixed with water may be filtrated, washed and, if desired, recrystalized to give crystalline dimeric monohydroxy aromatic compound.

The monohydroxy aromatic compound which can be dimerized according to the instant invention is a compound represented by formula [I]:

Ar—OH [I]

wherein Ar is an optionally substituted aromatic group. Examples of the aromatic groups may include phenyl, naphthyl, anthryl and pyrenyl.

Examples of the substituents may include halogen atom, halogenated lower alkyl, lower alkyl, lower alkoxy such as methoxy, phenyl, naphthyl, phenoxy, furyl, amino, toluidylamino, triadilamino, pyrimidylamino, benzoylamino, esterified carboxyl such as alkoxycabonyl and phenoxycarbonyl, amidized carboxyl such as phenylcarbamoyl, alkylaminosulfonyl, alkenyl of 2–6 carbon atoms which may include an aryl group.

When the substituent contains an aromatic ring, the compound may further have one or more substituents such as halogen atom, lower alkyl, lower alkoxy and phenyl groups on said aromatic ring.

In the present specification and claims, "lower" represents a group having 1–6 carbon atoms.

"Aromatic group" represents a 6-membered monocyclic aromatic group or condensed ring group consisting of up to 4 of 6-membered aromatic rings.

"Heterocyclic group having conjugated double bonds" represents a 5- or 6-membered mono-cyclic group or condensed ring group having at least one hetero-atom selected from N, S and O and conjugated double bonds. When it represents a condensed ring group, said group may have up to 6 rings.

In the present invention "dimerization" or "dimerizing" of a monohydroxy aromatic acid means forming a single bond between the aromatic rings at any position of the two-molecules by means of oxidation coupling reaction. The dimeric composition obtained by said reaction is recited as "dimer".

According to the present invention, examples of preferably dimerized monohydroxy aromatic compounds include phenol, naphthol and derivatives thereof.

The position of the bonding may differ among the compounds and for example, phenols or its derivatives bind at their o- or p-positions (Scheme 1).

α-naphthols and derivatives thereof bind at 2-positions of the naphthalene rings (scheme 2) and β-naphthols and derivatives thereof bind at their 1 or 3 positions (scheme 3).

(Scheme 1)

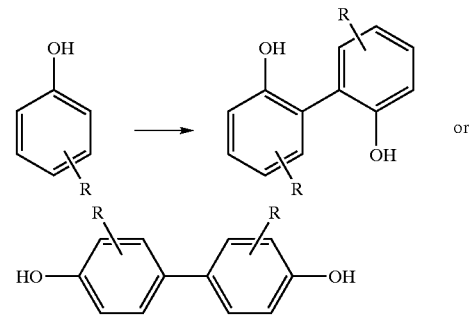

(Scheme 2)

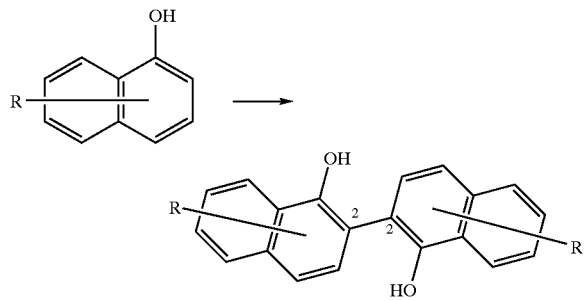

(Scheme 3)

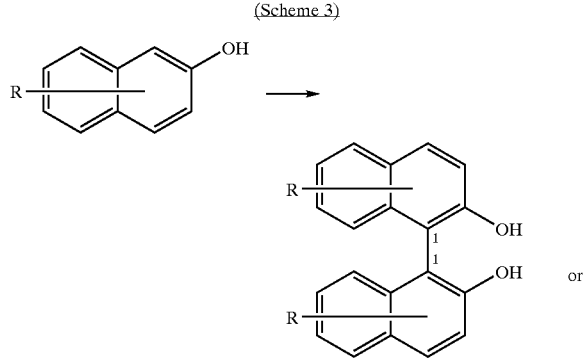

-continued

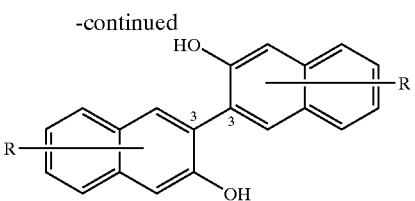

Further, after the single bonding is formed, some dimers of phenol derivatives and naphthol derivatives are further oxidized to give dimers wherein two monohydroxy aromatic compound molecules are bound by a double bond (schemes 4 and 5).

(Scheme 4)

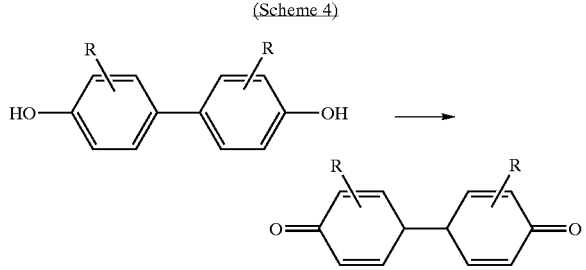

(Scheme 5)

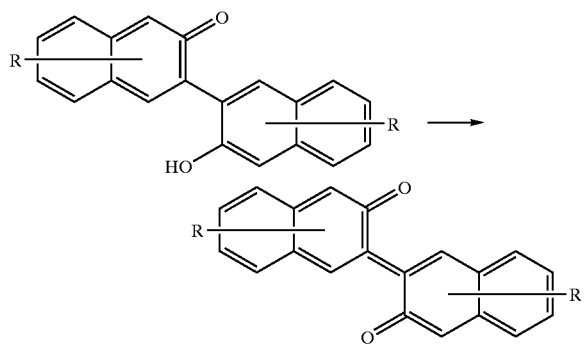

The instant invention also cover the dimers as above, which are dimerized by a double bond.

Especially preferable monohydroxy aromatic compound dimerized by the instant method is a compound represented by formula [II]:

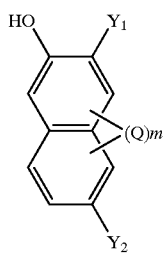

[II]

wherein $Y_1$ and $Y_2$ may be same or different and each is selected from the group consisting of hydrogen atom, an esterified carboxyl group, a group of —(CONH)n-X (wherein X is an optionally branched and optionally substituted hydrocarbon group which may have an unsaturated bond, an optionally substituted aromatic group or a heterocyclic group having conjugated double bonds, n is an integer of 1 or 2);

Q is selected from the group consisting of an optionally branched alkyl and alkoxy group of 1–6 carbon atoms, halogen atom, nitro group or nitroso group; and m represents an integer of 0–3.

Examples of preferred esterified carboxyl groups of $Y_1$ and $Y_2$ may include alkoxycarbonyl group of 1–6 carbon atoms, such as methoxycarbonyl, ethoxycarbonyl, propyloxycarbonyl, isopropyloxycarbonyl, butoxycarbonyl, tert-butoxycarbonyl, pentyloxycarbonyl and hexyloxycarbonyl groups, phenoxy carbonyl group and phenacyloxycarbonyl group. In case the group has an aromatic moiety, said moiety may have a substituent.

Examples of the optionally branched and optionally substituted hydrocarbon group which may have an unsaturated bond of X may include alkyl of 1–20 carbon atoms such as ethyl, butyl, octyl, dodecyl and octadecyl, alkenyl of 2–6 carbon atoms such as vinyl, allyl and pentenyl. Examples of the optionally substituted aromatic group of X may include, for example, phenyl, naphthyl, anthryl, anthraquinonyl and pyrenyl. Examples of the optionally substituted heterocyclic group having conjugated double bonds of X may include, for example, thiofuryl and furyl.

Examples of substituents in each definition may include those explained as substituents for Ar of formula [I].

In the present invention, the naphthalene ring of the formula [II] compound may have substituents of Q. The optional substituent Q may represent an optionally branched alkyl or alkoxy group of 1–6 carbon atoms, halogen atom, nitro or nitroso group.

The number of the substituent of m is usually 0 and may be up to 3.

The compound represented by formula [II], which is especially useful for the method of the instant invention, may be obtained by the following method:

Firstly, 2-hydroxynaphthalene-3,6-dicarboxylic acid may be obtained by the process according to WO98/17621 (Japanese patent Application No. 10-519205), that is, by reacting potassium 2-naphtholate and carbon dioxide, aciding out the reaction to obtain the compound and, if desired, purifying the same.

Then, an acid chloride of thus obtained 2-hydroxynaphthalene-3,6-dicarboxylic acid may be prepared by reacting with thionyl chloride or the like in a solvent such as xylene, tetrahydrofuran and sulfolane in a conventional manner, and then, may be treated with an amine to give the amide compound. Alternatively, 2-hydroxynaphthalene-3,6-dicarboxylic acid may be reacted directly with an amine in the presence of phosphorus trichloride or dicyclohexylcarbodiimide to give the amide compound.

An ester compound of formula [I] may be obtained by a conventional method, for example, by heating 2-hydroxynaphthalene-3,6-dicarboxylic acid in an alcohol in the presence of an acid catalyst.

Further, a compound of formula [I] wherein one of the substituents at 3- and 6-positions is an ester and the other is an amide may be obtained from 2-hydroxynaphthalene-3,6-dicarboxylic acid by means of the method described in WO96/32366. That is, condensation reaction of the naphthol derivative, 2-hydroxynaphthalene-3,6-dicarboxylic acid 3- or 6-mono ester and an aniline compound may be carried out. After that, water may be added thereto and then the reaction mixture may be neutralized and filtrated to give the desired compound.

The present invention is further described in reference to the following examples. The following examples are intended to illustrate the invention and are not to be construed to limit the scope of the invention.

EXAMPLE 1

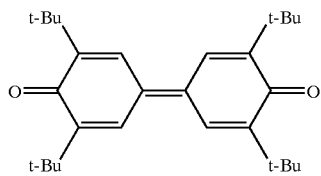

10.3 g of 2,6-di-t-butylphenol was dissolved in 100 g of N,N-dimethylformamide, 0.5 g of copper(I) chloride was added thereto and stirred at 60° C. The solution was heated for about 10 hours under air bubbling. The precipitates were collected by filtration, washed well with water and methanol and dried to give 9.6 g of brown crystal (decomposition point: 248° C., MS m/z 408 (MW=408.6)).

Figure 1:
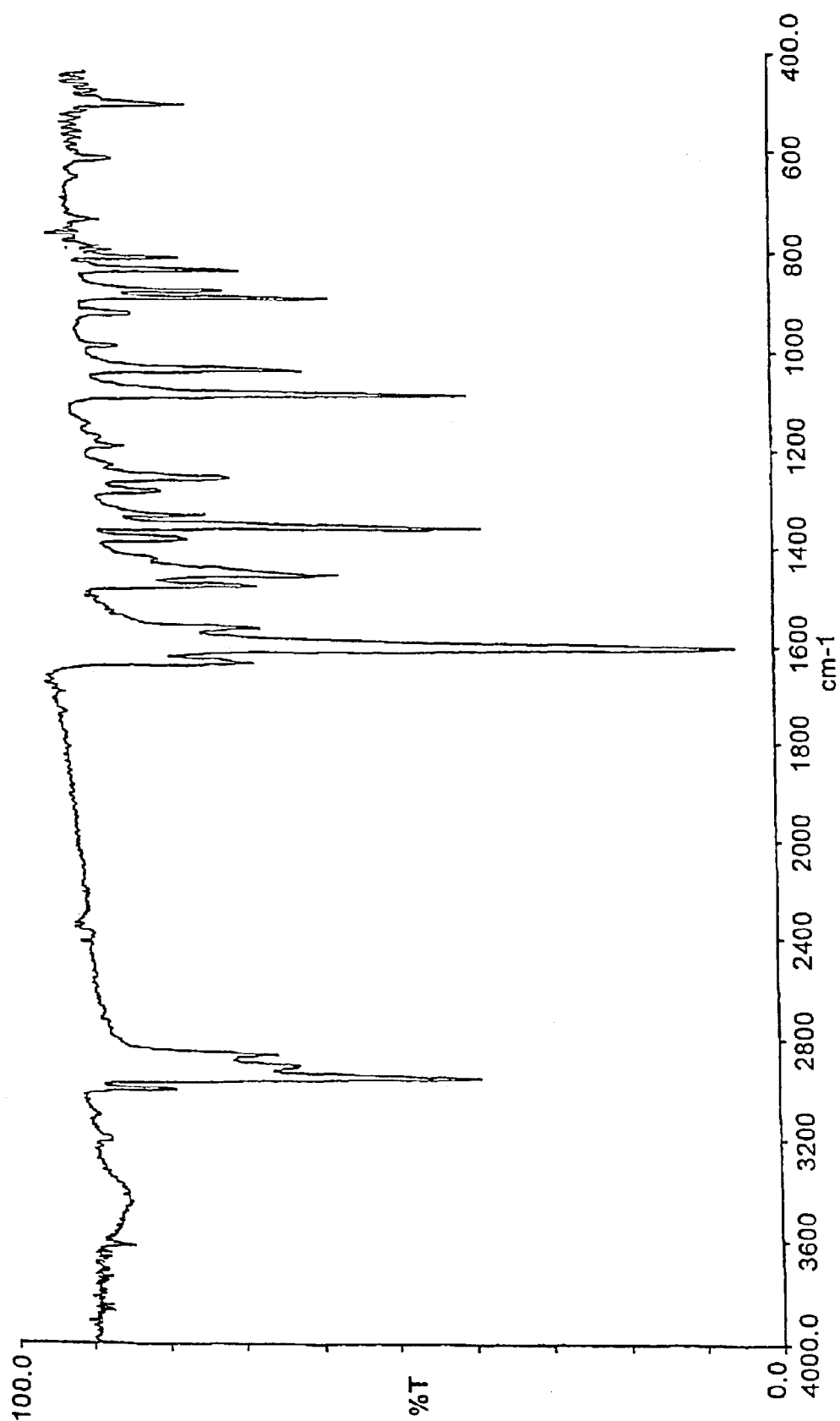
FIG. 1 is an infrared absorption spectrum (KBr) of the dimer obtained in Example 1.

The infrared absorption spectrum (KBr) of the dimer is shown in FIG. 1.

EXAMPLE 2

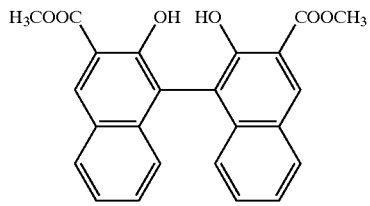

10.1 g of 2-hydroxy-3-methoxycarbonyl naphthalene was dissolved in 150 g of N,N-dimethylformamide, 0.5 g of copper(I) chloride was added thereto and stirred at 70° C. The solution was heated for about 18 hours under air bubbling. The reaction mixture was then poured into 500 g of water and the precipitates were collected by filtration. The precipitates were washed well with water and methanol and dried to give 9.4 g of yellow powder (melting point: 146° C., decomposition point: 339° C., MS: m/z 401 (MW=402.4)).

Figure 2:
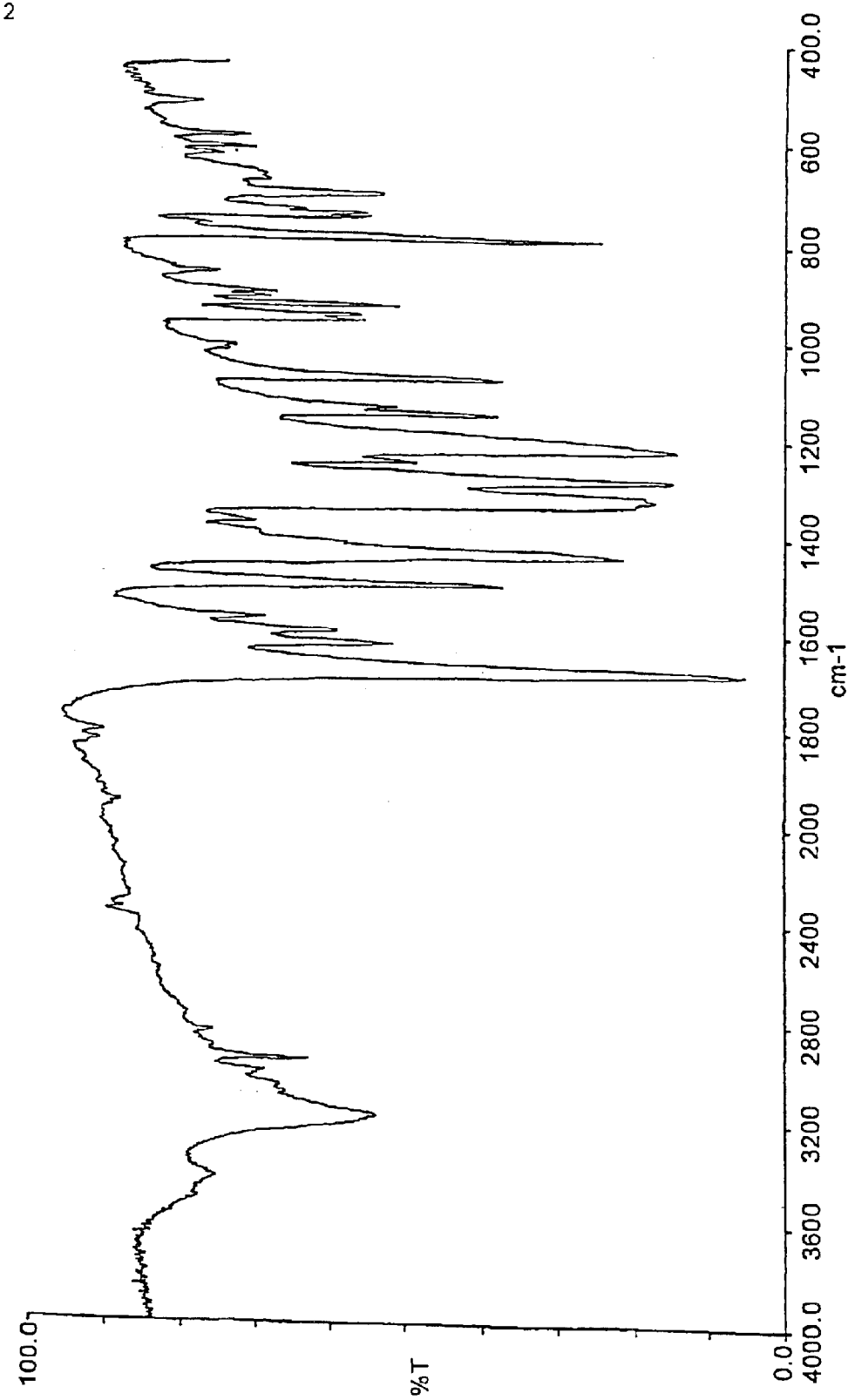
FIG. 2 is an infrared absorption spectrum (KBr) of the dimer obtained in Example 2.

The infrared absorption spectrum (KBr) of the dimer is shown in FIG. 2.

EXAMPLES 3–21

According to the same manner as described in Example 2 with the exception that phenol and naphthol derivatives shown in table 1 were used instead of 2-hydroxy-3-methoxycarbonylnaphthalene, dimers shown in table 1 were prepared. Mass spectroscopy data of the respective dimers are shown in table 1.

TABLE 1

| Ex. No. | phenol/naphthol | dimer | MS |
|---|---|---|---|
| 3 | | | m/z 408 |
| 4 | | | m/z 284 |
| 5 | | | m/z 286 |
| 6 | | | m/z 508 |

TABLE 1-continued
| Ex. No. | phenol/naphthol | dimer | MS |
|---|---|---|---|
| 7 | 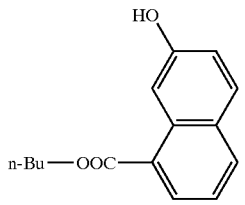 | 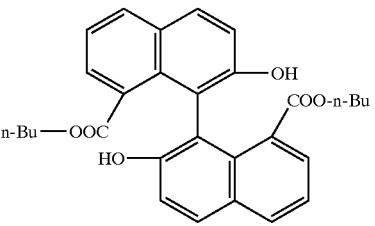 | m/z 486 |
| 8 | 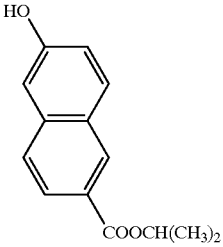 | 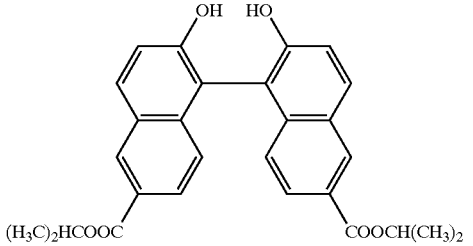 | m/z 458 |
| 9 | 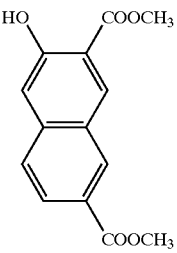 | 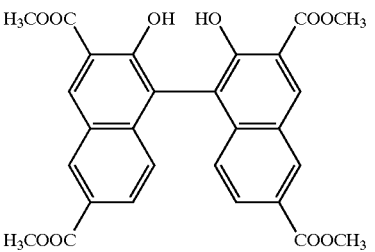 | m/z 517 |
| 10 | 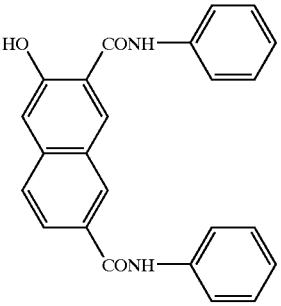 | 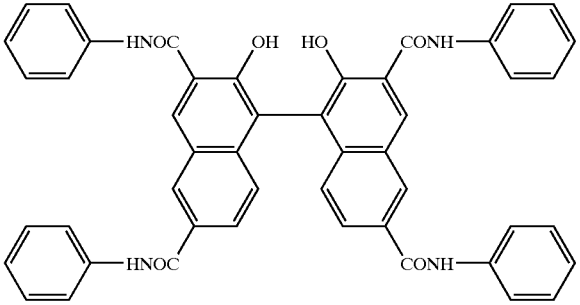 | m/z 761 |
| 11 | 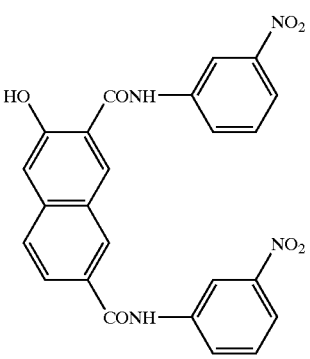 | 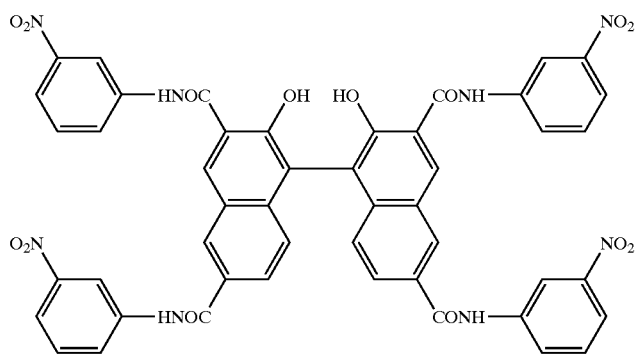 | m/z 943 |

TABLE 1-continued

| Ex. No. | phenol/naphthol | dimer | MS |
|---|---|---|---|
| 12 | | | m/z 974 |
| 13 | | | m/z 724 |
| 14 | | | m/z 823 |
| 15 | | | m/z 861 |
| 16 | | | m/z 1002 |

TABLE 1-continued

| Ex. No. | phenol/naphthol | dimer | MS |
|---|---|---|---|
| 17 | | | m/z 822 |
| 18 | | | m/z 918 |
| 19 | | | m/z 869 |
| 20 | | | m/z 1016 |

TABLE 1-continued

| Ex. No. | phenol/naphthol | dimer | MS |
|---|---|---|---|
| 21 | 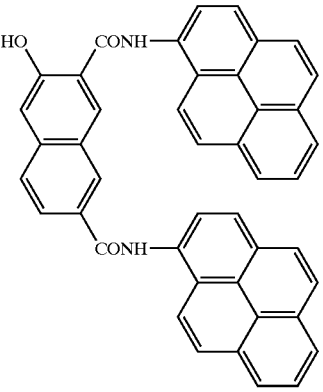 | 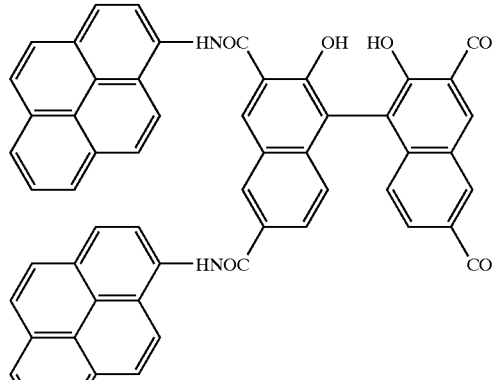 | m/z 1258 |

INDUSTRIAL APPLICABILITY

Dimers of the monohydroxy aromatic compound obtained by the present invention are useful for manufacturing antiseptic compounds or toning agents. According to the method of the present invention, dimer of a monohydroxy aromatic acid compound can be prepared in high yield with low cost.

What is claimed is:

1. A method for preparing dimer of a monohydroxy aromatic compound represented by formula: [II]

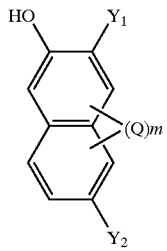

wherein $Y_1$ and $Y_2$ may be same or different and each is selected from the group consisting of hydrogen atom, an esterified carboxyl group, a group of —(CONH)n-X (wherein X is an optionally branched and optionally substituted hydrocarbon group which may have an unsaturated bond, an optionally substituted aromatic group or a heterocyclic group having conjugated double bonds, n is an integer of 1 or 2);

Q is selected from the group consisting of an optionally branched alkyl and alkoxy group of 1–6 carbon atoms, halogen atom, nitro group or nitroso group; and m represents an integer of 0–3;

comprising carrying out an oxidative coupling reaction of the monohydroxy aromatic compound in N,N-dimethylformamide solvent in the presence of a copper (I) salt.

2. The method of claim 1, wherein the oxidative coupling reaction is carried out in the presence of oxygen.

* * * * *